(12) United States Patent
Bhavsar

(10) Patent No.: US 11,506,614 B2
(45) Date of Patent: Nov. 22, 2022

(54) DEVICE FOR INSPECTION AND AUTHENTICATION OF GEMSTONES AND METHOD OF USING SAME

(71) Applicant: Shankar Ambadas Bhavsar, Troy, MI (US)

(72) Inventor: Shankar Ambadas Bhavsar, Troy, MI (US)

( * ) Notice: Subject to any disclaimer, the term of this patent is extended or adjusted under 35 U.S.C. 154(b) by 0 days.

(21) Appl. No.: 17/235,204

(22) Filed: Apr. 20, 2021

(65) Prior Publication Data

US 2021/0372935 A1 Dec. 2, 2021

Related U.S. Application Data

(60) Provisional application No. 63/012,504, filed on Apr. 20, 2020.

(51) Int. Cl.
*G01N 21/87* (2006.01)
*G01N 33/38* (2006.01)

(52) U.S. Cl.
CPC .......... *G01N 21/87* (2013.01); *G01N 33/381* (2013.01)

(58) Field of Classification Search
CPC ........ G01N 33/381; G01N 21/87; A45C 5/00; A45C 11/16
See application file for complete search history.

(56) References Cited

U.S. PATENT DOCUMENTS

| 4,275,810 | A | * | 6/1981 | Waldmeier | G09F 3/00 |
| | | | | | 206/459.5 |
| 2008/0179538 | A1 | * | 7/2008 | Shan | H01J 37/26 |
| | | | | | 250/442.11 |
| 2016/0174675 | A1 | * | 6/2016 | Bedman | A45C 11/16 |
| | | | | | 206/6.1 |

FOREIGN PATENT DOCUMENTS

| CN | 108749429 A | * | 11/2018 | |
| DE | 3307788 A | * | 9/1984 | B65D 85/00 |

* cited by examiner

*Primary Examiner* — Maurice C Smith
(74) *Attorney, Agent, or Firm* — Carrier, Blackman & Associates P.C.; Joseph P. Carrier; Fulchand P. Shende

(57) ABSTRACT

A device for inspection and authentication of gemstones (diamond pieces) includes a first member having a plurality of gemstone receiving portions, a second member having a plurality of diamonds covering portions which correspond to the gemstone receiving portions; each of the diamond covering portions having a viewing and inspection opening formed therein, a connection member disposed between end portions of the first and second members, a seal placement area formed on each of the first and second members; and an authentication seal configured to be placed on the seal placement area. The authentication seal is provided on the seal placement area without obstructing the viewing and inspection openings. The size of the viewing and inspection openings is less than size of gemstones placed in the gemstone receiving portion. The viewing and inspection opening includes one or more elongated portions for inserting a twizzer therethrough for holding and rotating diamond.

11 Claims, 7 Drawing Sheets

DEVICE FOR INSPECTION AND AUTHENTICATION OF GEMSTONES AND METHOD OF USING SAME

CROSS-REFERENCE TO RELATED APPLICATIONS

The present application claims priority under 35 USC § 119 to U.S. Provisional Patent Application No. 63/012,504, filed on Apr. 20, 2020. The entire subject matter of this priority document, including specification, claims and drawings thereof, is incorporated by reference herein.

BACKGROUND OF THE INVENTION

1. Field of the invention

The present invention relates to a device for inspection and authentication of gemstones, such as, diamonds, and to a method of inspection and authentication of gemstones using such device. More particularly, the present invention relates to a device for inspection and authentication of source of diamonds, which are natural or laboratory-grown mainly that of a plurality of gemstones including small, tiny gemstones, and/or other precious gemstones of small size, and to a method of inspection and authentication of the plurality of gemstones using such device.

2. Background Art

The gemstones, such as, diamonds which are naturally mined and processed, and are thus authentic, and which are further certified for their authenticity by authorized agencies are preferred by buyers including jewelers and consumers. In the last few years, the laboratories have been successful in manufacturing of diamonds which are laboratory-grown, artificial diamonds. It is known that there are no visible and/or optical differences between the natural and laboratory-grown diamonds. The optical differences between the natural and laboratory-grown diamonds cannot be found with the help of optical equipments, such as, jewelers' lenses, magnifying eye glasses, eye loupe, etc. The investors including, consumers prefer natural diamonds over the artificial diamonds for securing value of their investments. Since the differences between the natural and laboratory-grown diamonds are very subtle, only trained and skilled personnel at reputable institutes, agencies can conduct visual and detailed inspection using a sophisticate, technogically advanced (high-tech, expensive) machines, and provide certificate of genuineness of diamonds being natural.

In the world, the diamonds are generally certified for their genuineness by reputable institutes such as Gemological Institute of America (GIA) and its associated offices. The GIA operates in many countries around the globe and helps local jewelers for certification of authenticity of diamonds. The GIA is public benefit and a nonprofit institute. The GIA was established in 1931, and is the world's foremost certification authority on diamonds, colored stones, and pearls. Further, the GIA is a leader in knowledge, standards, and education in gemstones and jewelry industry.

The laboratory-grown gemstones, such as, diamonds are cheaper in cost compared to the natural diamonds. The natural diamonds are mined from earth. The mined diamonds are generally rough and do not have desired shape and sizes. Hence, the naturally occurring, mined diamonds are processed by cutting and polishing for obtaining optimal required sizes for making jewelry. This results in, for example, polished/cut gemstones are produced in a range of sizes from mined gemstones. So diamond dealers prefer to sell parcels containing gemstones in ranges of sizes which are not needed for the preparation of jewelry work piece, and thereby end up buying lot more than what is needed for the job at hand.

The further problem is that laboratory-grown diamonds, also referred as artificial diamonds or man-made diamonds, are identical in looks and most of the properties. Therefore, consumers, jewelers have to trust suppliers for genuineness of diamonds, particularly that of loose, small, tiny diamonds. The jewelers generally trust the suppliers and dealers based their honesty established during past dealings, general reputation and/or word of mouth. This is not a very desirable, productive way of doing business.

Further, the cost associated with inspection and authentication of big gemstones may be justified since big gemstones are generally marketed at desirable, higher prices. However, cost associated with inspection and authentication of individual small pieces of diamonds is not justified because the price of the small diamonds is less.

Further, with the advent of computer aided design (CM)) in making of articles of jewelry, which are considered to be elegant and fine, gemstones having specific sizes and shapes are required. For example, a certain jewelry article designed with CAD requires 1 mm size diamond pieces, in such proposed designed article of jewelry, 1 mm size diamond pieces are required to be and/or must be procured for proper manufacturing of the jewelry article. In such instances, the diamond pieces having size other than 1 mm, for example, diamond pieces having size of 1.2 mm may be of no use for the proposed design as it can not be replaced for 1 mm size diamond.

The present invention aims to overcome the disadvantages of the current method of relying on dealers for authentication of gemstones.

Accordingly, it is one of the objects of the present invention to provide a device and a method for inspection and authentication of diamonds, particularly source thereof, which is not dependent on trust and goodwill of the dealers and/or persons involved in transactions of diamonds particularly the small, tiny gemstones. Another object of the present invention is to provide a device and a method for inspection and authentication of diamonds of specific required sizes for the intended designs of jewelry articles.

SUMMARY OF THE INVENTION

In order to achieve the above objects, the present invention according to a first aspect thereof provides a device for inspection and authentication of gemstones. The device for inspection and authentication of gemstones according to the first aspect thereof includes a first member having a plurality of gemstone receiving portions, and a second member having a plurality of diamonds covering portions which correspond to the gemstone receiving portions of the first member. Each of the diamond covering portions has a viewing and inspection opening formed therein. The second member covers the first member such that the gemstones placed in the gemstone receiving portions are secured and an authentication seal is provided extending over the portions of the first member and the second member without obstructing inspection and viewing openings of the diamond covering portions.

The present invention according to another aspect thereof is characterized in that each of the plurality of gemstone receiving portions has a shape and a size corresponding to a shape and a size of a diamond piece to be received therein so that diamonds placed in the gemstone receiving portions are secured.

The present invention according to another aspect thereof is characterized in that each of the plurality of gemstone receiving portions has a concave shape. However, the shape of the gemstone receiving portions is not being limited to concave. Rather, a gemstone receiving portion may be any arrangement which receives and securely holds a gemstone therein.

The present invention according to another aspect thereof also provides a method for inspection and authentication of diamonds using the above discussed device.

The present invention according to another aspect thereof also provides a device for inspection and authentication of gemstones including a first member having a gemstone receiving portion configured to receive a gemstone therein; and a second member having a gemstone covering portion which correspond to the gemstone receiving portion of the first member. The gemstone covering portion has a viewing and inspection opening formed therein. The second member covers the first member such that an authentication seal is provided extending over portions of the first member and the second member without obstructing the viewing and inspection opening of the gemstone covering portion. A size of viewing and inspection opening is less than a size of the gemstone.

The present invention according to another aspect thereof provides a device for inspection and authentication of gemstones, including a first member having a plurality of gemstone receiving portions; each of the gemstone receiving portions configured to receive a gemstone including a diamond piece therein; and a second member having a plurality of gemstone covering portions which correspond to the gemstone receiving portions of the first member, each of the gemstone covering portions having a viewing and inspection opening formed therein. The second member covers the first member such that an authentication seal is provided extending over portions of the first member and the second member without obstructing the viewing and inspection openings of the gemstone covering portions. One or more of the viewing and inspection openings includes one or more elongated portions; and the elongated portions are configured to receive arms of a twizzer therein so that the diamond piece placed in the gemstone receiving portion is hold and rotated by tip ends of the twizzer for visual inspection of the diamond piece in its entirety.

For a more complete understanding of the present invention, the reader is referred to the following detailed description section, which should be read in conjunction with the accompanying drawings. Throughout the following detailed description and in the drawings, like numbers refer to like parts.

BRIEF DESCRIPTION OF THE DRAWINGS

FIGS. 4A-4C show several views of a device for inspection and authentication of gemstones; in which FIG. 4A shows views of the device in an open position including a front view, a top view, a left view and an isometric view thereof; FIG. 4B shows details of the first member including a front view, a left view and an isometric view thereof; and FIG. 4C shows details of the second member including a top view, a side view and an isometric view thereof.

DETAILED DESCRIPTION OF EXEMPLARY EMBODIMENTS OF THE INVENTION

Figure 1:
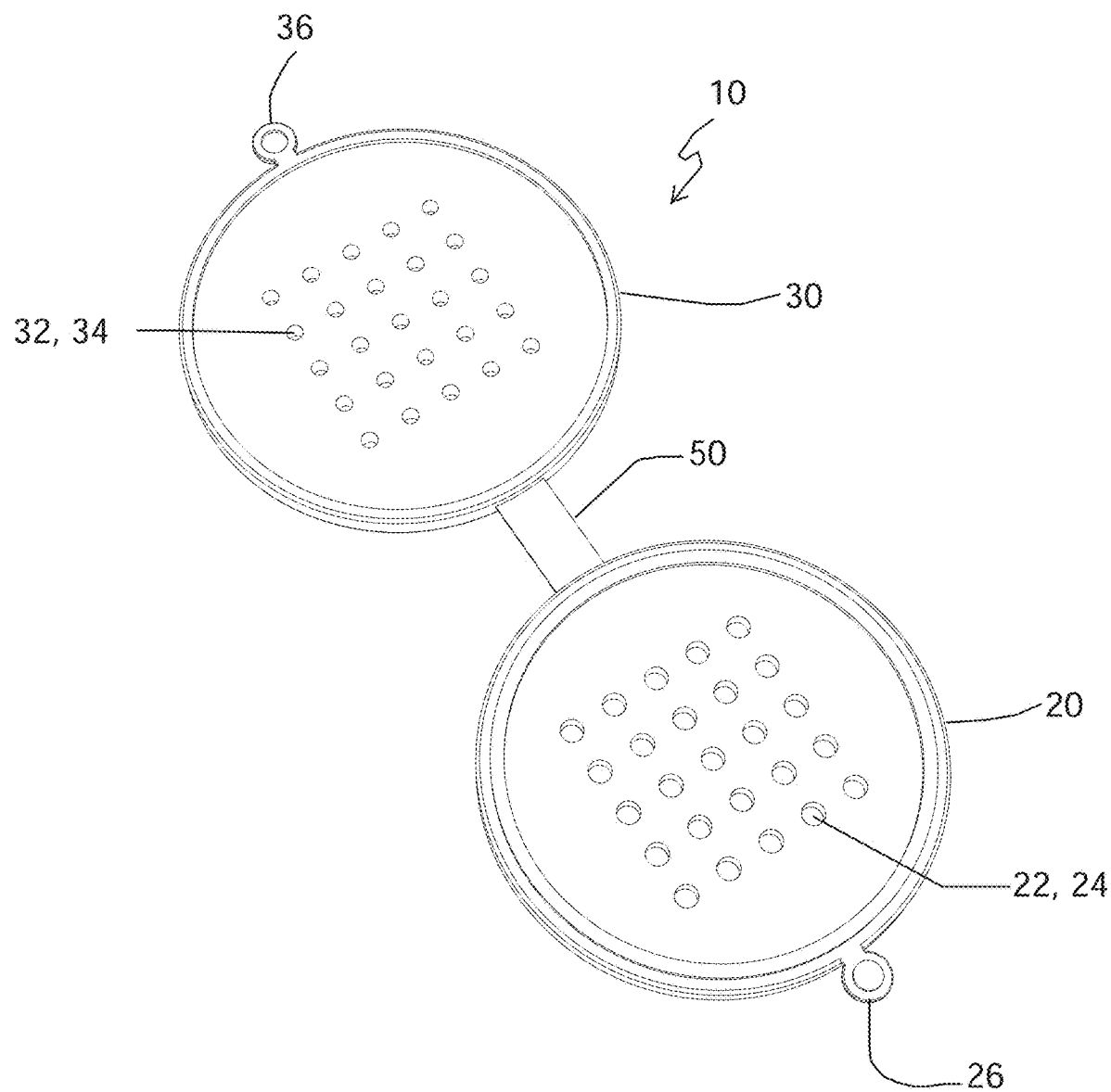
FIG. 1 is an exploded plan view in an opened state of a device for inspection and authentication of gemstones.
Figure 2:
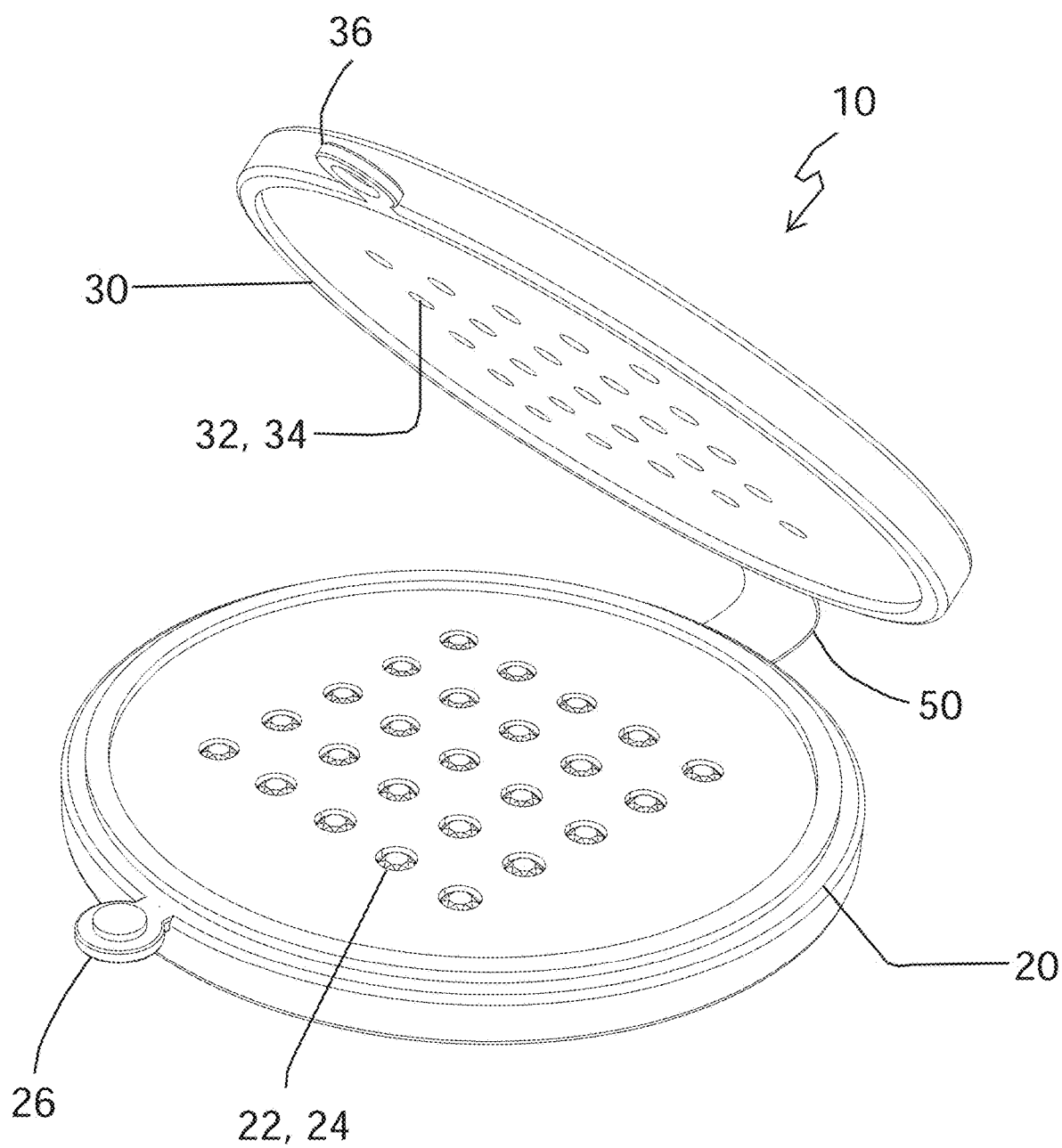
FIG. 2 is a perspective view the device for inspection and authentication of gemstones.

Various aspects of the device and method for inspection and authentication of diamonds are discussed below. In addition, various aspects diamonds including those of natural diamonds and laboratory-grown diamond are discussed.

Initially, it may be noted that there are two types of diamonds commercially used in making of jewelry—natural diamonds and laboratory-grown diamonds.

Natural versus Laboratory-Grown Diamonds

Both natural and laboratory-grown diamonds appear to be identical. Also, both the natural and laboratory-grown diamonds are crystal clear and give off a kaleidoscope of spectral colors in direct light. Natural diamonds are created by forces deep within the young Earth, and may be more than billion years old. Whereas, laboratory-grown diamonds are grown in a laboratory and do not have any age compared to natural diamonds. Nonetheless, laboratory-grown diamonds possess essentially the same chemical, physical and optical properties as natural diamonds.

According to the United States federal Trade Commission (US FTC), diamonds are essentially pure carbon. However, majority of natural diamonds contain trace amounts of nitrogen, which gives them a yellow color, or rarely boron, which imparts a blue color. In addition, natural diamonds usually contain inclusions, which are tiny bits of foreign material trapped in the still-forming diamond millions of years ago.

On the other hand, man-made, laboratory-grown, synthetic diamonds is a recent phenomenon and they are being produced in commercial quantities since last few years, five years or so.

Although laboratory-grown diamonds are identical in appearance to natural diamonds, there are very subtle differences between laboratory-grown and natural diamonds that can only be detected by trained gemologists and sophisticated equipment designed for that purpose, such as trained gemologists at GIA and sophisticated equipments available at GIA.

However, it is cost prohibitive to send small pieces of diamonds to GIA for testing to determine its characteristics and for determining whether that pieces of diamonds are natural or laboratory-grown.

Characteristics of Diamonds

According to GIA, generally accepted standards/characteristics for describing diamonds includes defining 4Cs, i.e., (1) color, (2) clarity, (3) cut and (4) carat weight thereof. Around the world, the universal method for assessing the quality of any diamond also generally includes defining/judging 4Cs—color, clarity, cut and carat weight of the diamond. The GIA creation of the Diamond 4Cs meant two very important things: diamond quality could be communicated in a universal language, and diamond customers could now know exactly what they were about to purchase.

Understanding what diamond color means helps in choosing the right diamond. Diamond color actually means lack of color. Accordingly, the diamond color evaluation of most diamonds is based on the absence of color. A chemically pure and structurally perfect diamond has no hue, like a drop of pure water, and consequently, a higher value. GIA has developed a D-to-Z diamond color-grading system (where D is the most colorless and Z is color), which measures the degree of colorlessness by comparing a stone under controlled lighting and precise viewing conditions to master stones of established color value. Many of these diamond color distinctions are so subtle that they are invisible to the untrained eye. However, these distinctions make a very big difference in diamond quality and price.

The clarity of diamond refers to the absence of inclusions and blemishes. It is well established that natural diamonds are the result of carbon exposed to tremendous heat and pressure deep in the earth. This naturally occurring process of diamond formation can result the diamond including a variety of internal characteristics, which are 'inclusions' and external characteristics, which are 'blemishes.' Generally, evaluation of diamond clarity involves determining the number, size, relief, nature, and position of inclusions and blemishes, and affect of the inclusions and blemishes on the overall appearance of the diamonds. Many inclusions and blemishes are too tiny to be seen by anyone other than a trained diamond grader, such as GIA certified graders.

The GIA diamond clarity scale has 6 categories, some of which are divided, for a total of 11 specific grades: (1) Flawless (FL)—No inclusions and no blemishes visible under 1.0× magnification; (2) Internally Flawless (IF)—No inclusions visible under 10× magnification; (3) Very, Very Slightly Included (VVS1 and VVS2)—Inclusions so slight they are difficult for a skilled grader to see under 10× magnification; (4) Very Slightly Included (VS1 and VS2)—Inclusions are observed with effort under 10× magnification, but can be characterized as minor; (5) Slightly Included (SI1 and SI2)—Inclusions are noticeable under 10× magnification; (6) Included (11, 12, and 13)—Inclusions are obvious under 10× magnification which may affect transparency and brilliance. In general, to the naked eye, a VS1 and an SI2 diamond may look exactly the same, but these diamonds are quite different in terms of overall quality. Therefore, expert and accurate assessment of diamond clarity is extremely important.

With regard to diamond cut, many often think of a diamond cut as shape (round, heart, oval, marquise, pear), but what diamond cut actually mean is how well a diamond's facets interact with light. It is known that diamonds are renowned for their ability to transmit light and sparkle so intensely. Precise artistry and workmanship are required to fashion a diamond stone so its proportions, symmetry and polish delivering the magnificent return of light in a diamond.

All of the diamond 4Cs, it is well recognized that cut is the most complex and technically difficult to analyze. There are five generally recognized categories of cuts, that is, (I) excellent, (ii) very good, (iii) good, (iv) fair, and (v) poor. Further, it is well understood that, cut is the only, one of the 4Cs, is in the hands of men.

In order to determine the cut grade of the standard round brilliant diamond—the shape that dominates the majority of diamond jewelry—calculation of the proportions of those facets that influence the diamond's face-up appearance is required. These proportions allow evaluation of what the best cut for a diamond is, by studying how successfully a diamond interacts with light to create desirable visual effects, such as, (1) Brightness—internal and external white light reflected from a diamond; (2) Fire-scattering of white light into all the colors of the rainbow; and (3) Scintillation—amount of sparkle a diamond produces, and the pattern of light and dark areas caused by reflections within the diamond.

Device for Inspection and Authentication Diamonds

As shown in FIG. 1, a device 10 for inspection and authentication of gemstones includes a first member 20 (also referred to as a lower member 20 or a female member 20), and a second member 30 (also referred to as upper member 20 or a male member 30) connected to the first member 20 at one end portion thereof using a connection member 50.

The connection member 50 may be integrally formed with the first member 20 and the second member 30 at one end portion thereof. Alternatively, the connection member 50 may include a hinge (not shown) which connects the first member 20 with the second member 30 at one end portion thereof. In another embodiment, the first member 20 and second member 30 may be separately formed and the connection member 50 such as an adhesive tape (not shown) may be later applied for joining the first member 20 with the second member 30 subsequent to the inspection the gemstones contained in the first member 20.

The first member 20 may have any desired shape, for example, a circular shape, a rectangular shape or irregular shape. The first member may be formed of a high quality plastic material, or any other suitable material including metal and/or glass.

The first member 20 is generally a plate-shaped, planer member. The first member 20 includes a plurality of gemstone receiving portions 22 formed therein. In another embodiment, the first member 20 may include only one gemstone receiving portion 22.

The gemstone receiving portions 22 include concave shaped cavities formed in the planar member. The gemstone receiving portions 22 having concave shape may be termed as female portions which are configured to receive and contain gemstones 24 therein. In another embodiment, the gemstone receiving portions 22 may include diamond holding structures formed in or on the first member 20. The gemstone receiving portions 22 have shapes and sizes corresponding to shapes and sizes of gemstones 24 to be placed therein. The gemstone receiving portions 22 are arranged in formed on the first member 20 in one of regular pattern, an irregular pattern and a combination thereof.

The second member 30 has a plurality of diamonds covering portions 32 which correspond to the gemstone receiving portions 22 of the first member 20. Each of the diamond covering portions 32 has a viewing and inspection opening 34 formed therein. The diamond covering portions 32 may have a convex shape, concave shape or a planer shape. The diamond covering portion 32 having convex shape may be termed as male portions which are configured to cover and protect the gemstones 24 contained in the gemstone receiving portions 22.

The size of the viewing and inspection opening 34 is less than the size of the gemstone receiving portion 22 and the gemstone covering portion 32 such that when the gemstone 24 is contained in the gemstone receiving portion 22 and covered by the respective gemstone covering portion 34, the gemstone 24 contained in the gemstone receiving portion 22 does not pass through/fall through the viewing and inspection opening 34 while the viewing and inspection opening 34 allows viewing and inspection of the gemstone 24 contained in the gemstone receiving portion 22.

In another embodiment, the gemstone receiving portion 22 may have an inspection opening formed therein. Yet in another embodiment, each the gemstone receiving portion 22 and the diamond covering portions 32 has a viewing and inspection openings formed therein. The viewing and inspection opening 34 formed in the gemstone covering portion 32 is also termed as a first viewing and inspection opening 34. The viewing and inspection opening (now shown) formed in the gemstone receiving portion 22 is a so termed as a second viewing and inspection opening. In such embodiment, the diamond piece contained in the gemstone receiving portion 22 may be inspected and viewed either from the second viewing and inspection opening formed in the gemstone receiving portion 22 or the first viewing and inspection opening 34 formed in the diamond covering portion 32, or from both the inspection openings of the gemstone receiving portions 22 and the diamond covering portions 32.

Further in another embodiment, as shown in FIGS. 4A-4C and FIG. 5, a device for inspection and authentication of gemstones includes a first member having a plurality of gemstone receiving portions; each of said gemstone receiving portions configured to receive a gemstone including a diamond piece therein; and a second member having a plurality of gemstone covering portions which correspond to the gemstone receiving portions of the first member, each of said gemstone covering portions having a viewing and inspection opening formed therein. The second member covers the first member such that an authentication seal is provided extending over portions of the first member and the second member without obstructing the viewing and inspection openings of the gemstone covering portions. The one or more of the viewing and inspection openings includes one or more elongated portions, which are configured to receive arms of a twizzer therein so that the diamond piece placed in the gemstone receiving portion is hold and rotated by tip ends of the twizzer for visual inspection of the diamond piece in its entirety.

In the embodiments shown in FIGS. 4A-4C and 5, tip ends of a twizzer can hold and also rotate a girdle portion of the diamond piece for visual inspection of the diamond piece in its entirety. In other words, this allows 100% visual inspection of the diamond pieces without removing them from the device while keeping the device completely sealed. It may be noted that the girdle portion of the diamond piece is a thin perimeter of the diamond piece.

The size and shape of the viewing and inspection openings shown in FIGS. 4A-4C and 5 is configured such that the diamond piece arranged in the gemstone receiving portion does not come out through the viewing and inspection opening while allowing the twizzer arms and tips to pass through the elongated portions (for holding and rotating the diamond piece for visual inspection of the diamond piece.

Accordingly, if the size (e.g., diameter) of the diamond piece is 4.0 mm, a central portion size of the viewing and inspection openings having elongated portions is less than 4.0 mm, e.g., 3.9 mm. The central portion size of the viewing and inspection opening is formed by and includes inner corner portions of the elongated portions at a peripheral portion thereof.

A seal placement area 26. 36 formed on each of the first member 20 and the second member 30. As shown in FIG. 1, the seal placement area 26, 36 may extend over portions of the first member 20 and the second member 30. In another embodiment, an additional seal placement area 26, 36 is formed over the connection portion.

Yet in another embodiment, the seal placement area 26, 36 may include each of the first member 20 and the second member 30 having an extension including a groove portion which allows the authentication seal and/or cord to be inserted therethrough.)

Figure 3:
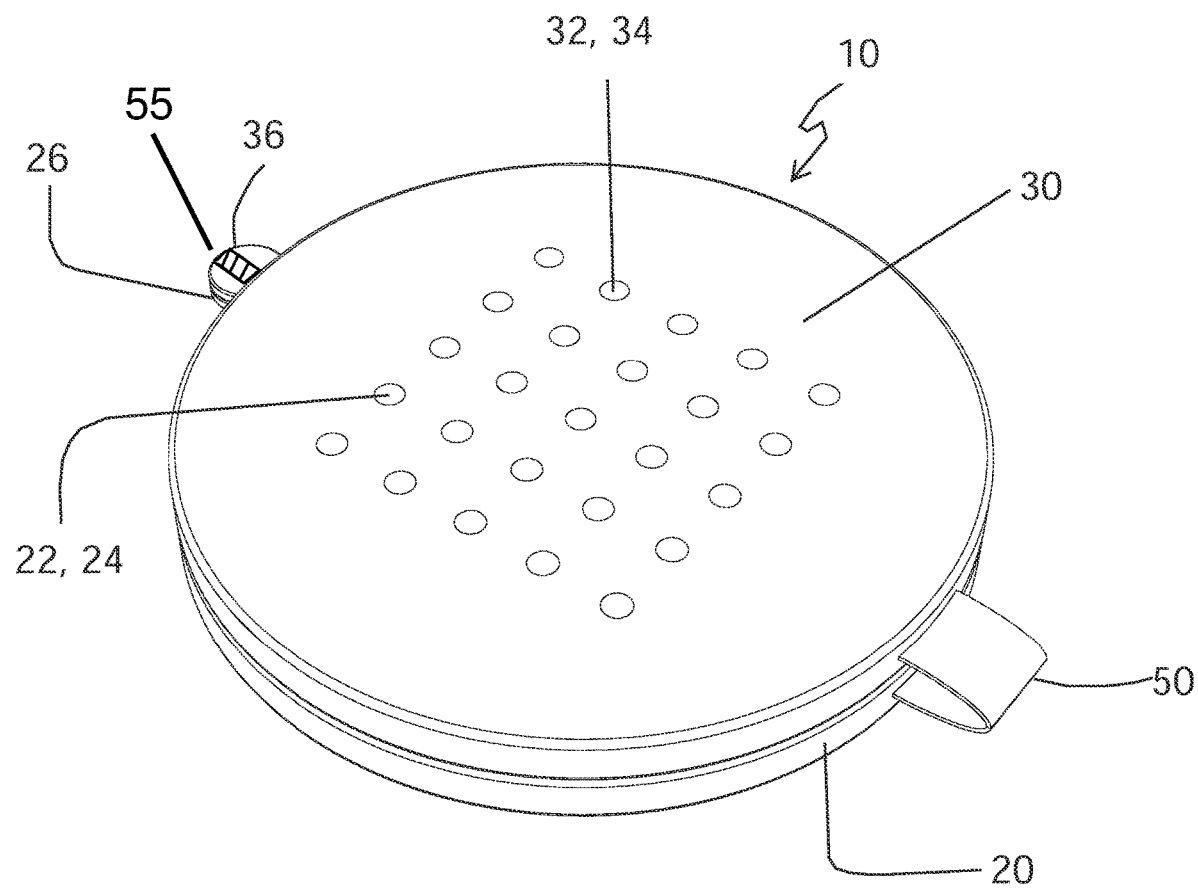
FIG. 3 is view of the device for inspection and authentication of gemstones in a closed state thereof.
Figure 4A:
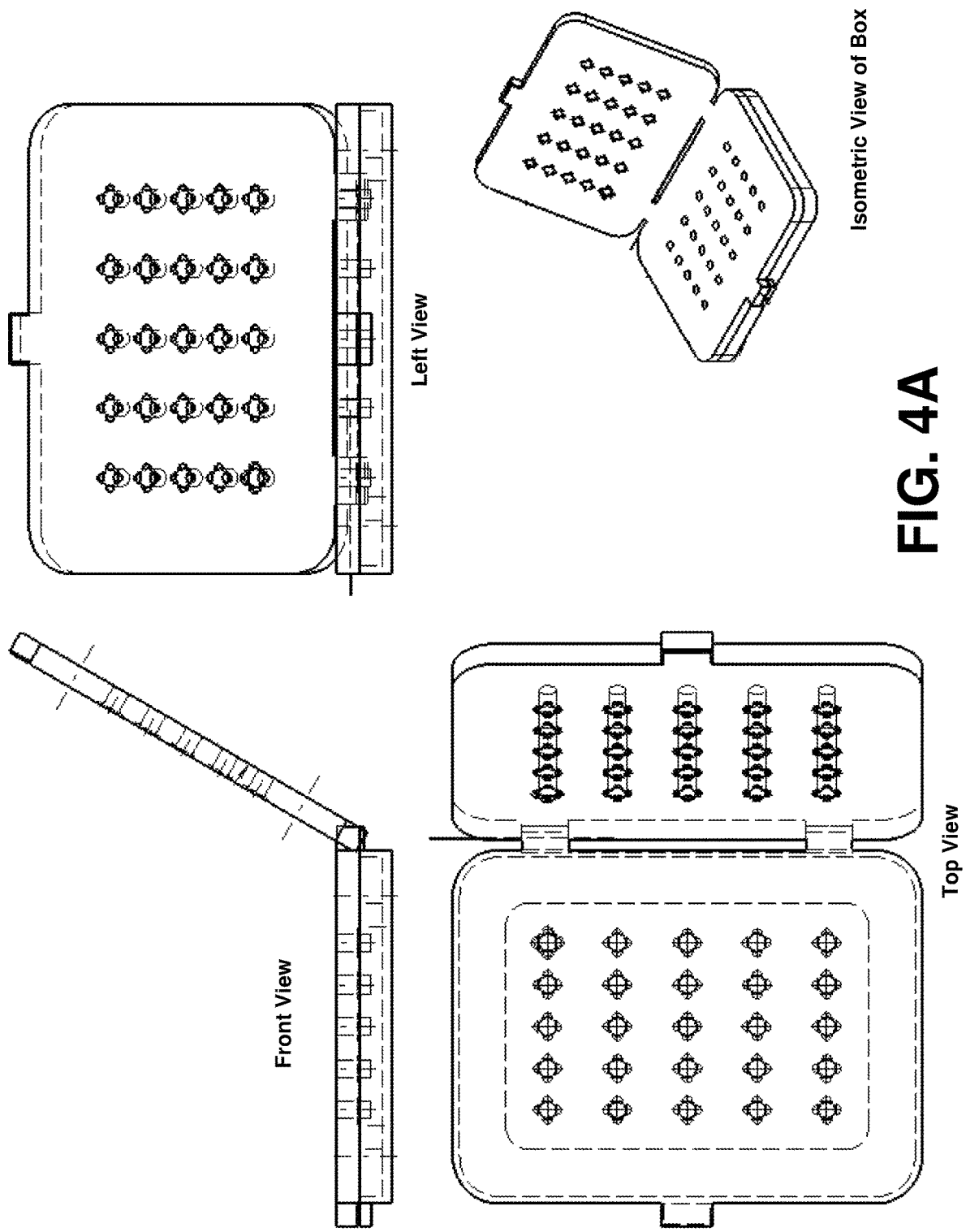
Figure 4B:
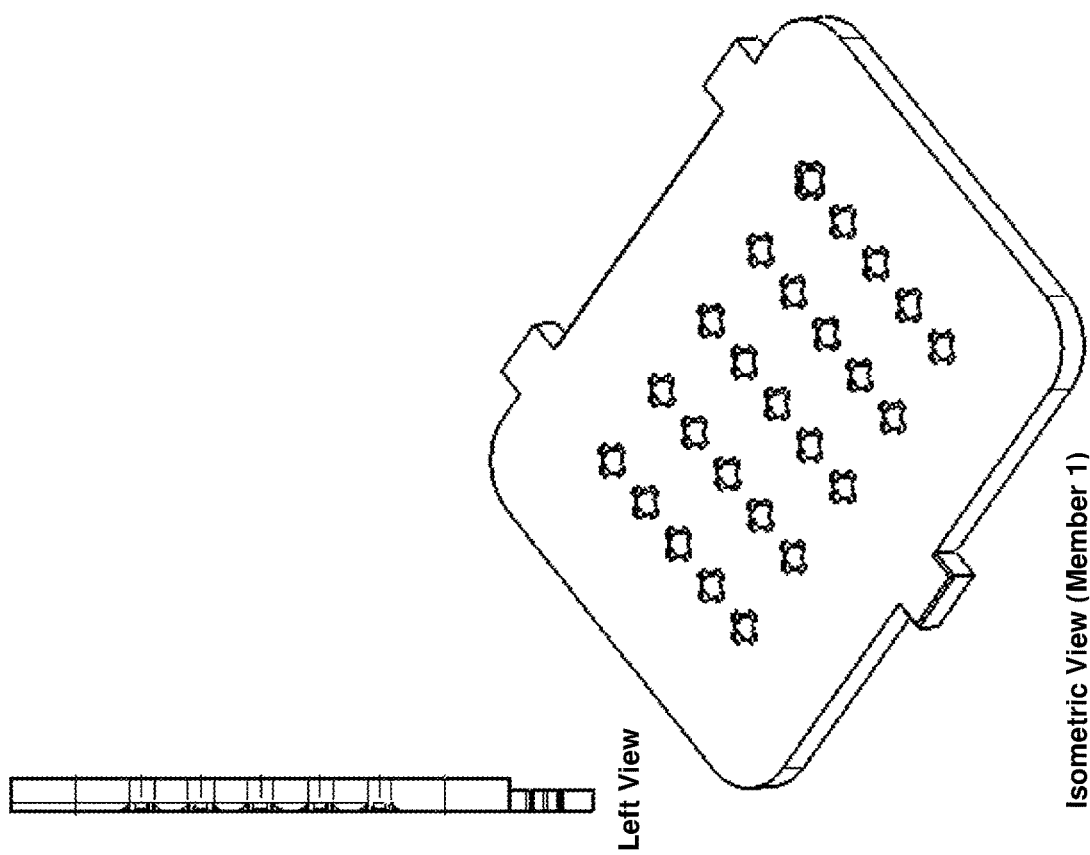
Figure 4B:
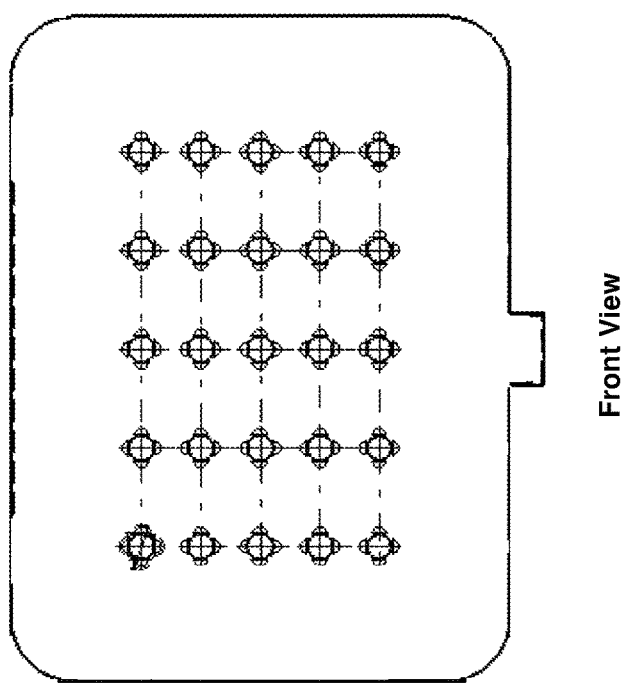
Figure 4C:
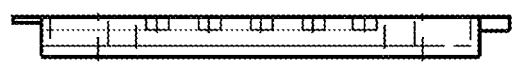
Figure 4C:
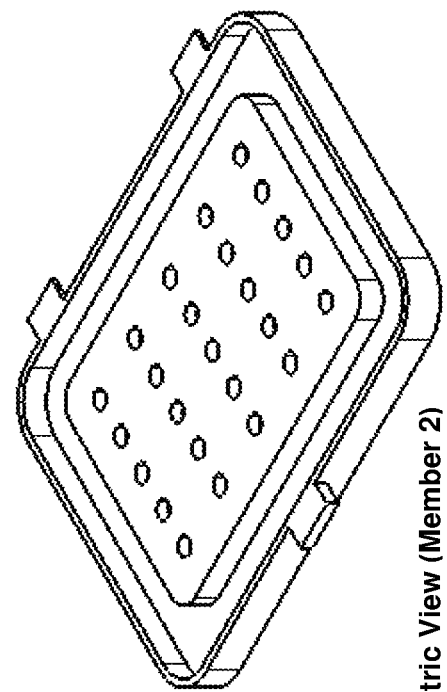
Figure 4C:
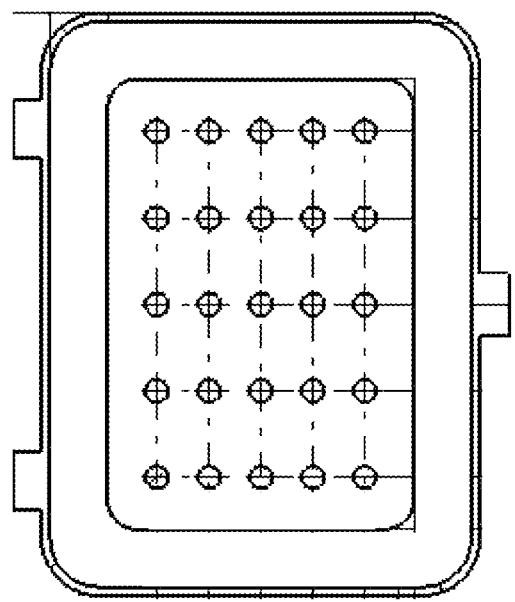
Figure 5:
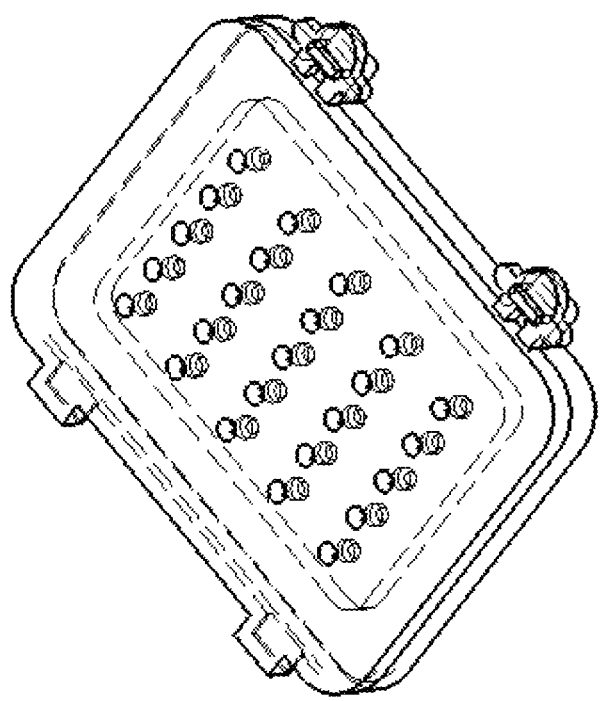
FIG. 5 is a perspective view of a device for inspection and authentication of gemstones taken bottom portion thereof.

An authentication seal 55 in FIG. 3 is placed on the seal placement area without obstructing viewing and inspection openings 34 of the gemstone covering portions 32 thereby allowing inspection and viewing of the gemstones contained in the gemstone receiving portions 22 through the viewing and inspection openings 34. Although the gemstones are inspected and viewed through the inspection openings 34, the gemstones contained in the diamonds receiving portions cannot be retrieved without breaking the authentication seal. The size of the inspection opening 34 is always less than the size of gemstones contained in the diamonds receiving portions 22.

Further once the authentication seal broken opened, the authentication seal cannot be placed back on to the first member 20 and second member 30 so as to avoid tampering of the authenticated gemstones contained in the diamonds receiving portions.

The presence/application of authentication seal on the diamond inspection device 10 is an assurance by the authorized agency that the gemstones contained in the device are of desired quality and source, e.g., natural diamonds.

The authentication seal is placed on the seal placement area by an authorized agency, such as Gemological institute of America (GIA). The authentication seals may bear the GIA emblem, inspection number and date of inspection, quality of gemstones. Additional certificate of inspection describing all characteristic aspects of the gemstones may be included.

Method for Inspection and Authentication of Gemstones

The method inspection and authentication of gemstones, such as, diamonds using a device 10 having a first member 20 and a second member 30 connected to the first member 20 at one end portion thereof using a connection member 50, includes the method steps of obtaining the device 10 having a desired number of gemstone receiving portions formed in the first member, each gemstone receiving portion being identified by a symbol, a number or a code, or a combination thereof; placing gemstones one each in respective gemstone receiving portions; covering the first member with the second member having gemstone covering portions each gemstone covering potion having a viewing and inspection opening formed therein, the diamond viewing and inspection opening having a size smaller than size of corresponding gemstone placed in the gemstone receiving portions; locking the first member and the second member so that diamond placed in the gemstone receiving portions of the first member are secured; delivering the device to the testing and inspection agency including Gemological Institute of America (GIA); getting testing and inspection of the gemstones contained in the device and preparing report of characteristics of gemstones by the GIA; getting certification including report of authentication of gemstones from the GIA; getting an authentication seal applied on to the device by GIA without obstructing the viewing and inspection openings. The seal may bear the GIA report number.

Once the GIA or other accepted laboratories, suppliers seal the device and the sealed device is sent to a vendor. The vendor send the perspective buyer, e.g., a jeweler, a manufacturer of diamond jewelry, the perspective buyer is assured that the diamonds contained in the device are genuine, i.e., naturally occurring diamonds.

A perspective buyer can view and inspect any or all of the gemstones contained in the device using convention methods, by using, jewelers lens, without opening the GIA seal. The viewing and inspection opening formed in the second member facilitates viewing and inspection of any or all of the gemstones contained in the device. If the authentication seal broken opened, the authentication seal cannot be placed hack so as to avoid tampering of the inspected and authenticated diamonds contained in the device.

In other words, a device for inspection and authentication of gemstones, includes a first member; a second member; a connection member 50 disposed between end portions of the first member 20 and the second member 30; a seal placement area formed on each of the first member and the second member; an authentication seal configured to be arranged on the seal placement area.

The first member 20 has a plurality of gemstone receiving portions 22, each of the gemstone receiving portions has a shape and a size corresponding to a diamond piece to be placed therein. The gemstone receiving portion generally has a concave shape. According the gemstone receiving portion may be termed as a female portion. The gemstone receiving portions may be arranged in one of regular pattern, irregular pattern and a combination thereof. The first member which includes gemstone receiving portion may be termed as a female member.

The second member includes a plurality of diamonds covering portions, which correspond to the gemstone receiving portions of the first member. Each of the diamond covering portions having a viewing and inspection opening formed therein. The diamond covering portion may have a convex shape or concave shape, or may be a simply planar profile. The diamond covering portion is a male portion. The first member which includes diamond covering portions may be termed as a male member.

A size of the inspection opening is less than the size of the gemstone receiving portion. In another embodiment, both of the gemstone receiving portion and said diamond covering portions may have a viewing and inspection opening formed therein The connection member is disposed between end portions of the first member and the second member. The connection member may be a hinge. The connection member may be continuously formed between the first member and the second member.

The seal placement area is formed on each of the first member and the second member. The seal placement area extends over portions of the first member and the second member. The seal placement area may include each of the first member and the second member having an extension having a groove portion which allows the authentication seal to be inserted therethrough, or various other methods of sealing gemstones.

The authentication seal configured to be arranged on the seal placement area. The authentication seal is placed on the seal placement area by an authorized agency, such as, Gemological Institute of America (GIA), and bears the GIA seal, inspection number and date of inspection, and/or supplier's own seal with guarantees.

The second member covers the first member such that the gemstones placed in the gemstone receiving portions are secured therein.

The authentication seal is provided on the seal placement area without obstructing inspection openings of the diamond covering portions thereby allowing inspection and viewing of the diamond placed in the gemstone receiving portions through the inspection openings. The diamonds placed in the diamonds receiving portions cannot be retrieved without breaking the authentication seal. In addition, if said authentication seal broken/opened, said authentication seal cannot be placed back so as to avoid tampering of the authenticated diamonds. The placement of the authentication seal on the device is an assurance by the authorized agency that the diamonds contained in said device are natural diamonds.

Advantageous Effects of the Present Invention

The present invention provides a device and system with zero risk for authenticating and transacting natural gemstones.

Further, in this contemporary age of digital technology, computer aided designs (CAD) is rampant and widely used in manufacturing jewelry resulting in a must requirement of specific sizes in millimeter (mm) and fractions thereof for gemstones. The present invention meets this requirement by providing gemstones of desired sizes, e.g. exact mm sizes. The diamond receiving portions in the first member can be customized according to requirement of diamond sizes for a specific CAD designed jewelry articles.

Secondly, lab grown diamonds and other gemstones are flooded in the mainstream market place making it almost impossible to verify whether the previous stone is natural or lab grown without using high tech expensive instruments by small jewelers and dealers, specially when jewelers are scattered in local cities around the world living them vulnerable to buy from only few of very expensive suppliers. In many cases, they get the gemstones which are not natural but looks a likes similar to naturals ones in color, clarity, cuts and carat weight, but are lab grown or simulated variation thereof. This makes jewelers and/or supplied vulnerable to law suits for frauds from consumer community without their own knowledge of whether the gemstones being lab grown. Similarly, if retail jeweler returns gemstones for any reason to suppliers, the suppliers have to make sure that they are receiving the natural stones only, if they are giving the natural stones and while getting returns. The present invention solves this issue by applying strict measures of authentication and sealing of the device with an authentication seal.

Currently, there are no exact, viable and/or desirable solutions to solve this huge problem in the precious stones industry. Whatever the solutions available, are consuming lots time and money, and are available to very few top businesses those are in position to secure big investments and resources needed.

The device of present invention is the cheapest, easiest and easy to understand/implement solutions available to solve many problems including required sizes, e.g., mm sizes and/or fractions thereof because of CAD technology needs, and secondly avoiding mixing of or providing lab grown instead of natural gemstones by suppliers or retailers while returning.

It is desirable to have a device that is safe, secured which helps remove the concerns of malpractices in handling of precious gemstones even when gemstones are moved back and forth at long distances, e.g., between different cities around the world, from parties involved. Furthermore, it would also be desirable to have a device that saves time and money. The present invention achieves such objectives. Still further it would be desirable to have a device affordable to everyone avoiding the needs of verifying authenticity of gemstone every time it exchanges the hands.

The disclosed device and associated method advantageously fill these needs and addresses the aforementioned deficiencies by providing an simple, easy to understand and use by all manufacturers to consumers at large.

The present invention provides a hassle free, minimal risk or may be zero risk, huge time/money savings device. The device is generally made up of the following components: two transparent members/plates, such as those made of material containing plastic, the first member/bottom plate having one or more stone sized cavities formed therein, the second member/top plate hinged with the first member, and having a slight smaller holes (inspection and viewing openings) than size of the stone/shape and having sufficient extended space around sides of girdles of device for necessity of sealing after the diamonds are placed in the bottom plate.

Further, the device may also have one or more of the following: cavities in the bottom plate can have all different shapes and sizes of the gemstones. Similarly, the corresponding holes in second member have slight smaller holes of corresponding shapes and sizes. Also the basic materials of these two plates can be one or more of hard cover paper, plastic, metals in different looks with or without hinges using different sealing methods which are not limited to the embodiments disclosed herein.

Similarly, the associated method may also include one or more of the following steps for certification from different gem testing laboratories and or from supplier with double or triple layers of security with authorized signatures. It can also be encrypted with tracking numbers and global positioning system (GPS) chips for higher safety and security standards.

The disclosed device is advantageous when compared with other known devices and solutions because it provides: (1) Fair distant transactions, (2) saves lots of time and money, and (3) provides complete peace of mind to suppliers, wholesalers, retailers and most importantly consumers for years to come.

Similarly, the associated method is advantageous in that it (1) saves on cost of producing, (2) saves time and money, and (3) minimizes or eliminates cause of authenticity concerns between concerned parties.

Similarly, the disclosed method is advantageous when compared with other known processes and solutions in that it: (1) reduces heavy cost of investments, (2) it eliminates needs of sophisticated expertise, and (3) it overcomes distance transactions' poor viabilities.

The disclosed device is advantageous in that it is structurally different from other known devices or solutions. More specifically, the device is unique due: to the presence of (1) sealed arrangements which can be seen, felt, verified and tested, (2) it is very affordable, and (3) provides distant transactions possibilities with low cost of per transaction.

Furthermore, the method associated with the aforementioned device is likewise advantageous. More specifically, the disclosed method/process owes its advantageousness to the fact that it can be done by distantly with low cost, zero or minimal risk for suppliers and consumers before and after commitments to buy or buys, and (3) guarantees of authenticities by involved parties starting from manufacturers to consumers including all intermediaries.

Again, the present invention is directed to device and system with zero risk for transacting natural gemstones between businesses, retailer and consumers.

As stated above, the device is generally made up of the following components. A pair of transparent plates, which may be made of very clear plastic, glass or metals, hinged with each others with similar sizes and shapes having extended sides for the purpose of sealing. A lower plate first member has holes/cavities for gemstones to sit therein accordance with their shapes and sizes, and an upper plate/ second member have a slight smaller holes of corresponding shape and size so the gemstone can not rattle, or move out of the cavity/grove formed in the bottom plate, and gemstones can be touched, felt and verified for authenticity from the upper plate without removing or replacing the authentication seal.

These two components—first member and second member—are connected by hinges as follows. The upper plate (second member) sits on bottom plate (first member) with same shape n size having enough extensions so that it can be sealed after the gemstones are place on bottom plate respective cavities formed in the bottom plate. It should further be noted that these plates dare of almost same sizes having three important needs: (1) gemstones sits in respective cavities so can not move out and get mixed with other gemstones, if they are more than one also gemstones can be viewed touch felt and inspected with other inspection/ verification devices by touching with tips of device without removing the sealed status thereby avoiding any types of malpractice of switching/replacing the gemstones in the device with lower quality gemstones.

According to one embodiment, a form of performing the method associated with the disclosed device generally consists of the following steps: (1) placing the gemstone in bottom plate in specific size and shape cavity; (2) shutting down upper plate tight such that all gemstones are viewed without removing this upper plate: and (3) sealing both the plates jointly such that gemstones cannot be removed without breaking the seal.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by this disclosure. It is indeed intended that the scope of this disclosure should be determined by a proper legal interpretation and construction of the disclosure, including equivalents, as understood by those of skill in the art relying upon the complete disclosure present at the time of filing.

Again, although the present invention has been described herein with respect to a number of specific illustrative embodiments, the foregoing description is intended to illustrate, rather than to limit the invention. Those skilled in the art will realize that many modifications of the illustrative embodiment could be made which would be operable. All such modifications, which are within the scope of the claims, are intended to be within the scope and spirit of the present invention.

What is claimed is:

1. A device for inspection and authentication of diamonds and other gemstones comprising:
   a first member having a plurality of gemstone receiving portions; each of said gemstone receiving portions configured to receive a gemstone therein; and
   a second member having a plurality of gemstone covering portions which correspond to the gemstone receiving portions of the first member, each of said gemstone covering portions having a viewing and inspection opening formed therein;
   wherein size of each of the viewing and inspection openings is less than size of a smallest one of the gemstones to be arranged in the gemstone receiving portion;
   wherein the second member covers the first member such that:
   an authentication seal is provided extending over portions of the first member and the second member without obstructing the viewing and inspection openings of the gemstone covering portions;

wherein one or more of the viewing and inspection openings includes one or more elongated portions; and wherein the elongated portions are configured to receive arms of a tweezer therein so that the diamond piece placed in the gemstone receiving portion can be held and rotated by tip ends of the tweezer for visual inspection of the diamond piece in its entirety.

2. The device for inspection and authentication of diamonds according to claim 1, wherein each of the plurality of gemstone receiving portions has a shape corresponding to a shape of a diamond piece to be received therein.

3. A device for inspection and authentication of diamonds according to claim 1, wherein each of the plurality of gemstone receiving portions has a concave shape.

4. A device for inspection and authentication of diamonds according to claim 1, wherein each of the plurality of gemstone receiving portions is configured to secure a diamond piece placed therein.

5. The device for inspection and authentication of diamonds and gemstones according to claim 1, wherein all viewing and inspection openings are the same size.

6. The device for inspection and authentication of diamonds and gemstones according to claim 1, wherein only one viewing and inspection opening is defined for each gemstone covering portion of the second member.

7. The device for inspection and authentication of diamonds gemstones according to claim 1, wherein the first member has no viewing and inspection opening defined therein.

8. A device for inspection and authentication of gemstones, comprising a first member having a plurality of gemstone receiving portions; each of said gemstone receiving portions configured to receive a gemstone including a diamond piece therein; and a second member having a plurality of gemstone covering portions which correspond to the gemstone receiving portions of the first member, each of said gemstone covering portions having a viewing and inspection opening formed therein;

wherein:

the second member covers the first member such that an authentication seal is provided extending over portions of the first member and the second member without obstructing the viewing and inspection openings of the gemstone covering portions;

one or more of the viewing and inspection openings includes one or more elongated portions; and the elongated portions are configured to receive arms of a tweezer therein so that the diamond piece placed in the gemstone receiving portion is held and rotated by tip ends of the tweezer for visual inspection of the diamond piece in its entirety.

9. The device for inspection and authentication of gemstones according to claim 7, wherein a girdle portion of the diamond piece is held and rotated by tip ends of the tweezer for visual inspection of the diamond piece in its entirety.

10. The device for inspection and authentication of gemstones according to claim 9, wherein the girdle portion of the diamond piece is a thin perimeter of the diamond piece.

11. The device for inspection and authentication of gemstones according to claim 7, wherein size and shape of the viewing and inspection opening is configured such that the diamond piece arranged in the gemstone receiving portion does not come out through the viewing and inspection opening while allowing the tweezer arms and tips to pass therethrough for holding and rotating the diamond piece for visual inspection of the diamond piece.

* * * * *